(12) United States Patent
Park et al.

(10) Patent No.: US 10,363,052 B2
(45) Date of Patent: Jul. 30, 2019

(54) SYSTEM FOR PERFORMING AN ARTHROPLASTY PROCEDURE ON A PATIENT BONE

(71) Applicant: Howmedica Osteonics Corporation, Mahwah, NJ (US)

(72) Inventors: Ilwhan Park, Walnut Creek, CA (US); Lacerial Pearson, Livermore, CA (US); Stephen M. Samuel, San Jose, CA (US)

(73) Assignee: Howmedica Osteonics Corporation, Mahwah, NJ (US)

( * ) Notice: Subject to any disclaimer, the term of this patent is extended or adjusted under 35 U.S.C. 154(b) by 0 days.

(21) Appl. No.: 16/242,813

(22) Filed: Jan. 8, 2019

(65) Prior Publication Data

US 2019/0142440 A1 May 16, 2019

Related U.S. Application Data

(60) Division of application No. 15/274,717, filed on Sep. 23, 2016, now Pat. No. 10,213,220, which is a
(Continued)

(51) Int. Cl.
*A61B 34/10* (2016.01)
*A61B 17/15* (2006.01)
(Continued)

(52) U.S. Cl.
CPC .......... *A61B 17/1764* (2013.01); *A61B 6/032* (2013.01); *A61B 17/154* (2013.01); *A61B 17/155* (2013.01); *A61B 17/157* (2013.01); *A61B 17/1668* (2013.01); *A61B 17/1675* (2013.01); *A61B 17/17* (2013.01); *A61B 17/171* (2013.01); *A61B 17/1703* (2013.01); *A61B 34/10* (2016.02); *A61F 2/30* (2013.01); *B29C 64/386* (2017.08); *B29C 64/393* (2017.08); *G05B 19/4099* (2013.01); *G06F 17/5009* (2013.01); *G16H 50/50* (2018.01);
(Continued)

(58) Field of Classification Search
CPC ........ A61B 2034/108; A61B 2034/105; A61B 2034/102; A61B 2017/568
See application file for complete search history.

(56) References Cited

U.S. PATENT DOCUMENTS

| 6,712,856 B1* | 3/2004 | Carignan | A61B 17/1764 623/20.35 |
| 7,258,701 B2* | 8/2007 | Aram | A61B 17/155 623/20.15 |
| 7,618,451 B2* | 11/2009 | Berez | A61B 5/1076 606/84 |

* cited by examiner

*Primary Examiner* — David W Bates
(74) *Attorney, Agent, or Firm* — Polsinelli PC

(57) ABSTRACT

A system for performing a total joint arthroplasty procedure on a patient's damaged bone region. A CT image or other suitable image is formed of the damaged bone surfaces, and location coordinate values $(x_n, y_n, z_n)$ are determined for a selected sequence of bone surface locations using the CT image data. A mathematical model $z = f(x,y)$ of a surface that accurately matches the bone surface coordinates at the selected bone slice locations, or matches surface normal vector components at selected bone surface locations, is determined. The model provides a production file from which a cutting jig and an implant device (optional), each patient-specific and having controllable alignment, are fabricated for the damaged bone by automated processing.

30 Claims, 10 Drawing Sheets

Related U.S. Application Data continuation of application No. 14/928,767, filed on Oct. 30, 2015, now Pat. No. 10,034,678, which is a continuation of application No. 14/869,762, filed on Sep. 29, 2015, now Pat. No. 10,226,261, which is a continuation of application No. 14/335,460, filed on Jul. 18, 2014, now Pat. No. 9,730,713, which is a continuation of application No. 13/730,608, filed on Dec. 28, 2012, now Pat. No. 8,882,779, which is a continuation of application No. 11/641,569, filed on Dec. 18, 2006, now Pat. No. 8,801,720, which is a continuation of application No. 10/146,862, filed on May 15, 2002, now abandoned.

(51) Int. Cl.
*A61B 17/17* (2006.01)
*A61B 6/03* (2006.01)
*A61F 2/30* (2006.01)
*A61B 17/16* (2006.01)
*G06F 17/50* (2006.01)
*G16H 50/50* (2018.01)
*B29C 64/386* (2017.01)
*B29C 64/393* (2017.01)
*G05B 19/4099* (2006.01)
*A61B 17/00* (2006.01)
*A61B 17/56* (2006.01)
*B33Y 50/00* (2015.01)
*B33Y 50/02* (2015.01)
*B33Y 80/00* (2015.01)
*A61B 90/00* (2016.01)

(52) U.S. Cl.
CPC . *A61B 17/1739* (2013.01); *A61B 2017/00526* (2013.01); *A61B 2017/568* (2013.01); *A61B 2034/102* (2016.02); *A61B 2034/104* (2016.02); *A61B 2034/105* (2016.02); *A61B 2034/108* (2016.02); *A61B 2090/3762* (2016.02); *B33Y 50/00* (2014.12); *B33Y 50/02* (2014.12); *B33Y 80/00* (2014.12); *G05B 2219/35134* (2013.01)

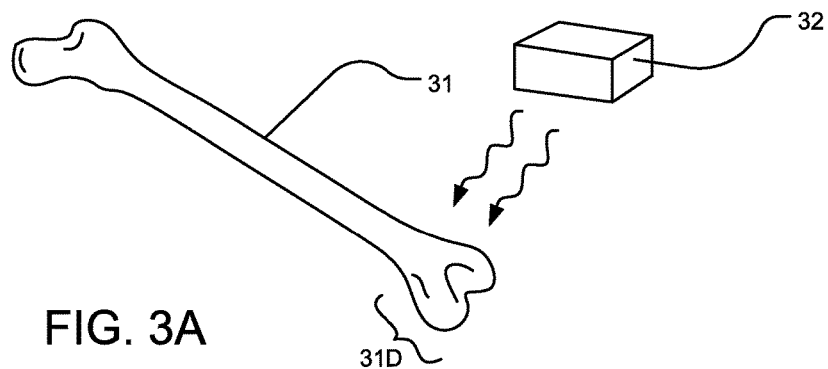
FIG. 3A
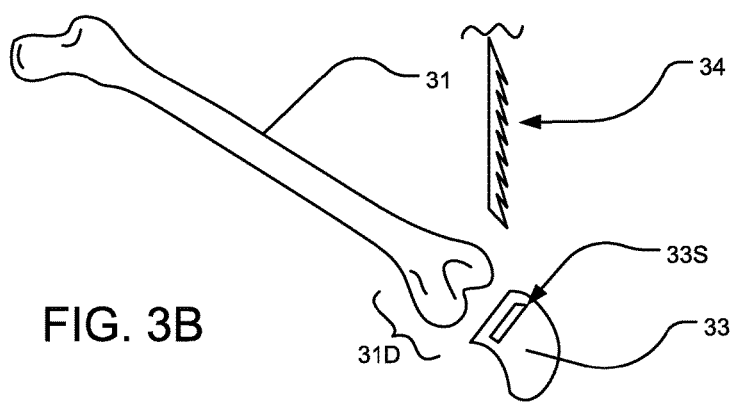
FIG. 3B
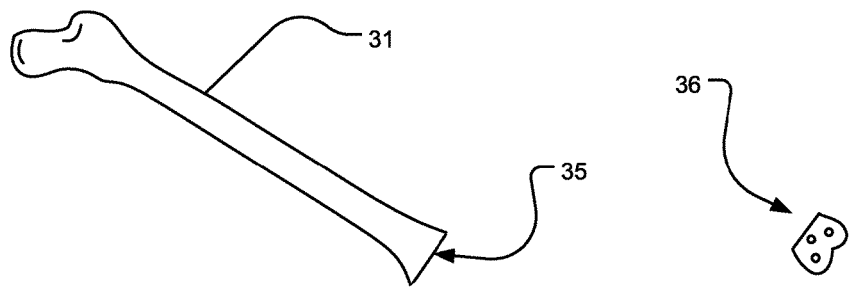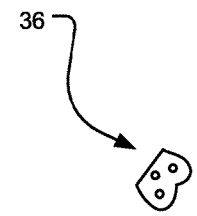
FIG. 3C  FIG. 3D

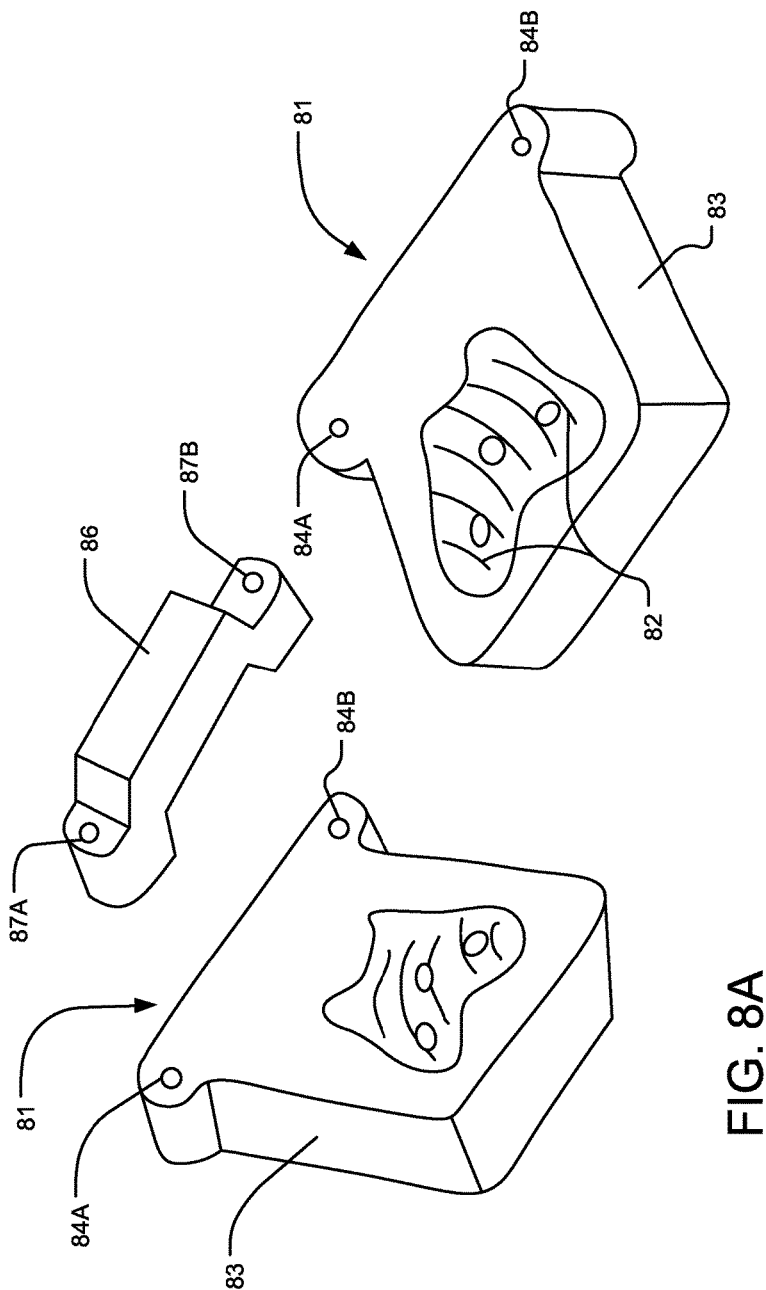

SYSTEM FOR PERFORMING AN ARTHROPLASTY PROCEDURE ON A PATIENT BONE

CROSS-REFERENCE TO RELATED APPLICATIONS

The present application is a divisional of U.S. application Ser. No. 15/274,717 filed Sep. 23, 2016, which application is a continuation of U.S. application Ser. No. 14/928,767 filed Oct. 30, 2015, now U.S. Pat. No. 10,034,678, which is a continuation application of U.S. application Ser. No. 14/869,762 filed Sep. 29, 2015, which is a continuation application of U.S. application Ser. No. 14/335,460 filed Jul. 18, 2014, now U.S. Pat. No. 9,730,713, which is a continuation of U.S. application Ser. No. 13/730,608 filed Dec. 28, 2012, now U.S. Pat. No. 8,882,779, which application is a continuation of Ser. No. 11/641,569 filed Dec. 18, 2006, now U.S. Pat. No. 8,801,720, which application is a continuation of U.S. application Ser. No. 10/146,862 filed May 15, 2002, abandoned. The above-referenced applications are incorporated by reference herein in their entireties for all that they disclose or teach.

FIELD OF THE INVENTION

This invention relates to fabricating a value added medical device for patient-specific, total joint arthroplasty (TJA) procedures. More specifically, the invention relates to a system for producing a value added medical device or instrument (collectively referred to as a "medical device" herein), based on computer tomography (CT) or other imaging of a region of the body adjacent to a selected joint.

BACKGROUND OF THE INVENTION

Surgeons are generally dexterous and highly trained to achieve a standardized level of surgical skill. However, surgeons have limitations, including a lack of micron-level geometric accuracy. For example, a surgeon cannot place an instrument at an exact, numerically defined location (within, say, 100 µm) relative to a patient's body part and then move the instrument through a defined trajectory. Many surgeons are unable to exert a precise, predefined force in a selected direction. Furthermore, a surgeon may have small hand tremors that limit his/her ability to operate on very small and delicate structures. Unfortunately, many of these limitations affect the outcome of certain surgical procedures, especially in cases where micron-level geometric accuracy is required. For example, the three-dimensional locations and directions of basic procedures used to modify a bone (including drilling, cutting, and reaming) determine the alignment and fit of the implant(s). These factors directly influence these functional outcomes.

Recently, to assist surgeons in overcoming these limitations, computer-assisted surgery (CAS) utilizing robotic- or image-guided technologies has been introduced into various medical fields. CAS, as a categorization or surgical technology, includes not only robotics but also image-guided surgical devices, surgical navigation systems, pre-operative planners, and surgical simulators.

A primary goal of CAS technologies is to integrate pre-operative planting with intra-operative performance. One of the most important steps in integrating preoperative medical images directly into operating room procedures is registration of image and corresponding body part(s). Registration is a computational procedure that matches pre-operative images or planning information to the position of the patient on the operating room table. Rigid pins or other fiducial markers were used in early systems, such as in a robot-assisted system.

For robot-assisted total knee alignment (TKA) surgery, illustrated in FIG. 1, two spaced apart pins, 11A and 11B, are fixed to a target bone 12 before CT images are formed of the damaged bone region 14. The phrase "CT imaging" or "CT scanning" will refer herein to any suitable two- or three-dimensional imaging procedure, including computer tomography, and magnetic resonance imaging. The pins, 11A and 11B, are used to allow alignment of a three-dimensional (3-D) reconstruction of the patient bone 12. The intraoperative locations of the pins are used to relate the position of the patient's bone to a pre-operative plan, using a robot controller 14.

Based upon a converted CT scan image of the exposed bone(s) in the damaged bone region, the location and angular orientation of the femoral mechanical axis (FMA), femoral anatomical axis (FAA) and tibial mechanical axis (TMA) are also determined, and a postoperative plan for orientation and movement of the milling machine 16 are determined in a coordinate system relative to the target bone 12, to mill the bone end according to a pre-programmed cutting file. After the registration process i.e., matching the CT image bone model with the target bone using the two pins, the robot assistant is activated, and the milling cutter attached to a robot arm mills the damaged bone region to create one (or preferably several) exposed planar surfaces (transverse, anterior, chamfer, etc.) to accept and mate with a femoral implant.

This method is accurate, to the extent that the ready-made implant device matches the patient's own bone surfaces, but requires at least two surgical operations (including incisions or cutting for each): a first operation for installation of a robotic calibration mechanism and a second operation for the final surgery to install the TKA device itself.

The second surgical operation is constrained by a tourniquet time limitation, which places a practical limit on a maximum cumulative time an open wound can be exposed (usually 90-120 min. for TKA) without severe danger of infection. This is another disadvantage of robot-assisted surgery, which requires use of a registration process and of a bone location fixation process, both time consuming. As compared to robot-assisted surgery, a conventional manual TKA procedure is usually completed in no more than 30 minutes, despite a relatively high probability of misalignment.

Shape-based registration, illustrated in FIG. 2, is an alternative method as shown in the previous art for TKA and THA that has been developed recently and currently used in clinical trials. A patent's damaged bone 21D is exposed, in a first surgical operation. A location coordinate sensor 22 is placed in contact with the damaged bone surface 21 at each of a selected sequence of spaced apart locations, and the coordinates of each such surface point are received by a location coordinate processor 23 for subsequent processing. The processor 23 provides an approximate equation for the surface of the damaged bone region 21D. At least 15 surface coordinate triples are selected and digitized on the actual bone surface, and the data are analyzed and processed to match, as closely as practicable, the CT scan image data, using interpolation, extrapolation and other suitable mathematical approximations. When a matching relation is found, optical or other sensors tack and guide a tracking device to provide a surgeon with the location and angular orientation information needed to identify a suitable implant device. For a TKA procedure, the image formation system guides and locates the tracking device to provide location and orientation of transverse, anterior chamfer cuts to fit the femoral implant.

Using the surface matching or registration technique illustrated in FIG. 2, the shapes of a model of the bone surface 21, generated from a pro operative image, are matched to surface data points identified during the first incision or during surgery. Intra-operative surface data points can be specified by direct contact with percutaneous probes, from within the surgical exposure using ultrasonic or direct-contact optical probes, or from fluoroscopic radiographic images. Location tracking is a critical step in CAS. Tracking devices are attached to a target bone and to my tools to be used during the operation, such as drills, reamers, guides, or screwdrivers. Many common tracking devices use optical cameras and infrared light emitting diodes. These optical sensors are easy to set up, very accurate, have fast sensing rates of up to 100 measurements per second, and can tack multiple tools simultaneously. A disadvantage of the devices illustrated in FIGS. 1 and 2 is that they require additional surgical time, require a direct line of sight to perform the procedure, require special training of surgeon and staff, require maintenance and frequent calibration of the robotic mechanism(s), and can be very expensive, depending on the required level of accuracy.

Other tracking technologies use acoustic or magnetic sensors that create an electromagnetic field around the surgical site that is altered as instruments move within the field. Such devices do not require a direct line of sight, but the devices may be less accurate, cannot be used with metallic tools, and have difficulties tracking multiple tools simultaneously. One major benefit of either of these tracking methods is a reduction in radiation, due to elimination of the need for intra-operative fluoroscopy or radiography to check component position.

The systems described in the preceding discussion often suffer from a lack of readiness for the operating room and do not always address practical considerations. Many systems introduce additional capital equipment, equipment maintenance and operative steps into the surgical procedures that prolong the surgery and require significant training. Further, most of the systems do not address the issues of sterility and safety, and unwanted motion of the body part(s) to be operated upon. Most systems require input from the surgeon in order to specify data or alter program flow. Many systems rely on a non-sterile assistant to enter data, using a keyboard, mouse or pen, but this is inefficient and risks miscommunication. A sterilized or draped input device, introduced into the surgical operating theater, may be difficult to use, may be distracting for the surgeon, requires the splitting of the surgeon's attention between the display screen in one location and the surgical tool in another, and requires removal of the tool from the surgical site for use elsewhere as an input device.

What is needed is a system that requires only one surgical procedure (defined as requiring at least one incision or cutting operation), employs a pre-operative scanning procedure that provides micron level accuracy, is flexible enough to account for certain tolerances relative to an idealized fit, and provides a fabricated, patient-specific cutting jig and a patient-specific (optional) implant device whose components can be aligned and altered according to the body part(s) involved.

SUMMARY OF THE INVENTION

The needs discussed in the preceding paragraph are met by the invention, which uses pre-operative scanning and construction of a geometric model of the target body part surface, pre-operative fabrication of a patient-specific cutting jig and a patient-specific (optional) implant device, which may have one or more than one component, monitoring and a correction of the jig and/or implant device, vis-a-vis the target body part, and relies on a single surgical procedure to remove a selected part of a damaged bone and to implant and initially test an implant device (optional) in vivo.

One feature of the invention is use of an image-based surgical system in total joint arthroplasty, such as total hip arthroplasty (THA), total knee arthroplasty (TKA), total elbow arthroplasty (TEA), spinal surgery, etc. The system software receives or provides geometrical information on the damaged bone, captured in CT or another suitable imaging format, and converts his information into a three-dimensional (3D) model of the bone surfaces during the computer-aided pre-operative planning. The converted 3-D model includes the information on corresponding bone dimensions along with the uncertainties associated with CT scanning and conversion errors. The system displays all the pertinent information on the damaged bones on the screen. The system provides a surgeon with improved visualization of the relationship between the damaged bone and the cutting jig or implant device, including but not limited to accurate alignment of the device, by accurately superimposing representations of a cutting jig and/or an implant device being used in the surgical field over the images of the bone.

Another feature of the invention is that, once the planning is complete, the system software prepares and provides a computer file to direct rapid production machines, such as a computer numerical control (CNC) machine, a stereo-lithograph (SLA) machine, etc., to fabricate a cutting jig and/or an implant device (optional), which may be disposable (replaceable) or non-disposable (recyclable). The value added cutting jig and/or implant device is made of any bio-compatible material and works with a manual and/or automated instrument to transfer joint planning information between a computer-aided pre-operative planning phase and the actual surgical procedure. During surgery, the cutting jig is employed to guide critical cuts and shaping of the bone, such as drilling, reaming, sawing, etc. The cutting jig and/or implant device (optional) includes a surface profile that matches the bone surfaces in vivo.

With reference to the cutting jig surface profile, guiding holes for drilling and inspection, a slot feature for a sawing process, and bushing features for reaming and drilling are fabricated. Alternatively, the surface profile can be created with reference to guiding holes, slots and bushings.

A related feature of the invention is that the system software performs virtual surface mapping techniques with respect to the 3D model based on CT scan images, including point-to-point mapping, surface normal vector mapping, and surface-to-surface mapping techniques. Depending on the application, one or a combination of mapping techniques can be employed.

Another feature of invention is that the system software includes transferring of all pre-operative planning data and related computer files to a production floor model through a selected communication system (e-mail, file transfer protocol, web-browser, LAN, fiber optic cable, wireless, etc. and/or manual transfer).

Another feature of the invention is that, upon receiving the data from a remote planning station, the system software automatically executes and provides information pertinent to the rapid production and inspection processes. A quality control procedure includes monitoring and verification of 1)

the surface profile of a cutting jig and of an (optional) surgical implant device compared to the 3-D profile of the bone virtual surface from the CT image and 2) Station and angular positioning of the fabricated features such as drilling holes, slots and bushings. Later, the jig and the (optional) implant device are cleaned, sterilized (optional), packaged and delivered to the surgical operating theater.

These features and advantages of the present invention are embodied in an improved system for assisting a surgeon in using a surgical tool to provide accurate cutting, implant positioning and alignment with respect to one or more body parts. The system uses a computer-aided calibration process involving a surface matching of the cutting jig and/or implant device to the bone surface(s). Because the cutting jig and/or implant device is fabricated using CT scan image data, there is no need for use of a registration process, expensive tracking systems or robotic systems in an operating room, or for use of two or more surgical procedures. The invention is designed rework in conjunction with any manual standard TJA instrumentation, and thus minimizes additional expenditures for capital equipment purchases. Furthermore, there is no increase in surgical time, and the cutting jig and/or implant device can provide a reduction in surgical time.

BRIEF DESCRIPTION OF THE DRAWINGS

FIG. 3A illustrates a damaged region of a target bone undergoing CT scan.

FIG. 3B illustrates the target bone as shown in FIG. 3A with a jig having a transversely oriented slot or aperture to accept a cutting instrument, such as a saw blade.

FIG. 3C illustrates the target bone as shown in FIG. 3A with the damaged region having been removed.

FIG. 3D illustrates a fabricated implant device.

DETAILED DESCRIPTION OF THE INVENTION

1) System Architecture

Figure 1:
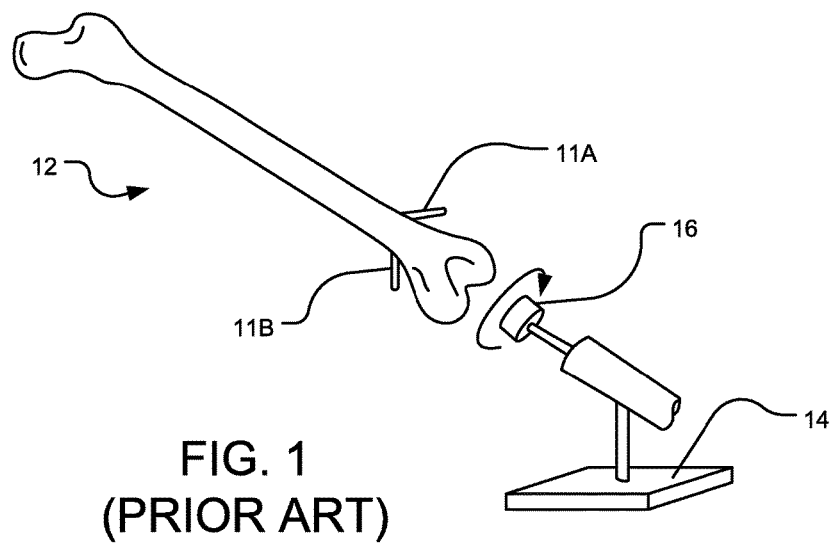
FIG. 1 illustrates robot-assisted total knee arthroplasty (TKA).
Figure 2:
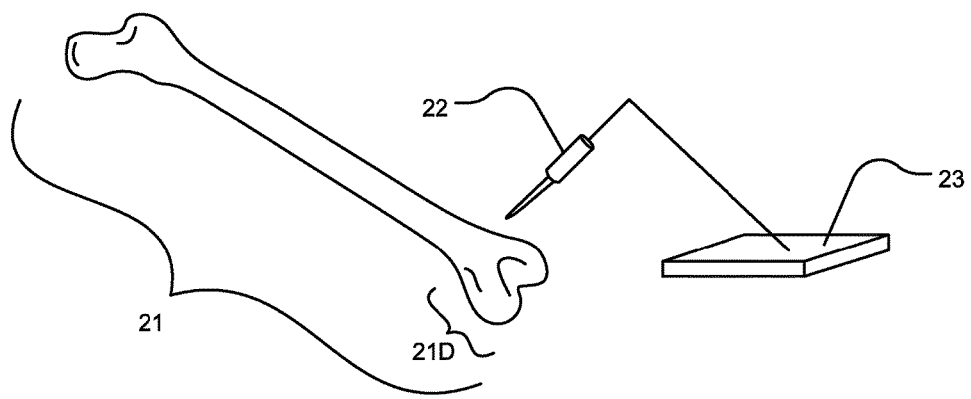
FIG. 2 illustrates shape-based registration in TKA.

In a preferred embodiment, the invention provides accurate positioning and alignment of an orthopedic implant without a significant increase in surgical time or capital equipment cost. Also, during the actual surgery, the system does not require use of registration, image matching or location tracking, which distinguishes the invention from other image-based systems.

FIGS. 3A, 3B, 3C and 3D illustrate some features of the invention. A damaged region 31D of a target bone 31 undergoes CT scan in FIG. 3A. Pre-operative planning is performed, using a computer and a CT image scanner 32, to construct a model of bone suffices adjacent to the damaged region 31D, with an associated inaccuracy of no more than 90 μm. Based on the accumulated planning data, a production file is created to receive the CT image data and to fabricate a jig or cutting block and, optionally, an implant device. The production file and the planning information are sent to the production floor for fabrication of a patient-specific jig and a corresponding implant device patient-specific or off-the-shelf.

In FIG. 3B, a jig 33 is fabricated to seat against the femur (or against the tibia, for tibia processing) and has a transversely oriented slot or aperture 33S that accepts and provides a guide for a cutting instrument 34, such as a reciprocating saw blade. After incision in the patient's body, the cutting instrument 34 would be placed in and aligned with the slot 33S so that, when the cutting instrument is activated and the femur (or tibia) is exposed, a distal end portion of the femur (or proximal end portion of the tibia) can be removed to provide a planar exposed surface 35, as illustrated in FIG. 3C.

Note that no incision into or cutting of the patient's body has yet occurred; the jig 33 and slot 33S are designed and fabricated using primarily the information obtained from the CT image scan. An implant device 36, illustrated in FIG. 3D and having a planar surface, is optionally fabricated from the CT scan information, without incision into or cutting of the patient's body.

The fabricated jig 33 and optional implant device 36 are delivered to a surgical operating theater, and the patient's body is cut open to expose at least the distal end of the femur 31 and the proximal end of the tibia in the damaged bone region 31D. The jig 33 and slot 33S are positioned, and a member of the surgical team removes a portion of the distal end of the femur 31 (and, similarly, removes a portion of the proximal end of the tibia) to provide an exposed and aligned planar surface 35 (and, similarly, to provide an exposed and aligned planar surface of the tibia). The femur jig 33 is then removed, and a corresponding planar surface of the femur implant device 36 is optionally attached to the exposed planar surface of the femur distal. This attachment may be done using one, two, three or more attachment mechanisms, such as bolts, screws or nails, that attach the femur implant device 36 to the remainder of the distal end of the femur, at the femur planar surface 35. In a similar manner, a tibia implant device is attached to the remainder of the proximal end of the tibia at the tibia planar surface.

During the surgery, the custom mating between the jig 33 and the remainder of the target bone (femur and/or tibia) at the exposed planar surface ensures a precise fit (location and alignment, drilling holes and a slot 33S) for surgeons in performing the joint repair/replacement process with any manual standard instrumentation.

Figure 4A:
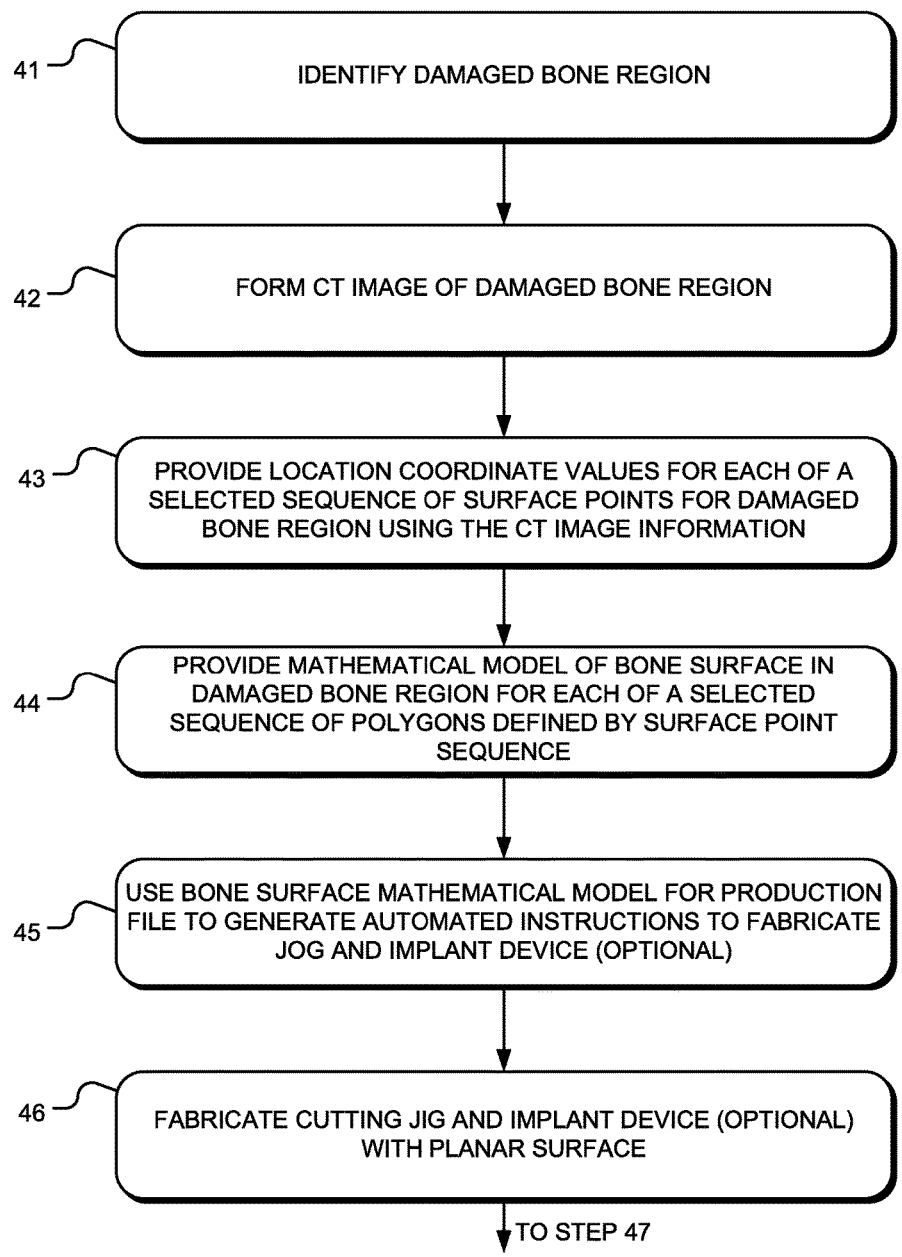
FIGS. 4A/4B are a flow chart of a procedure for practicing the invention.
Figure 4B:
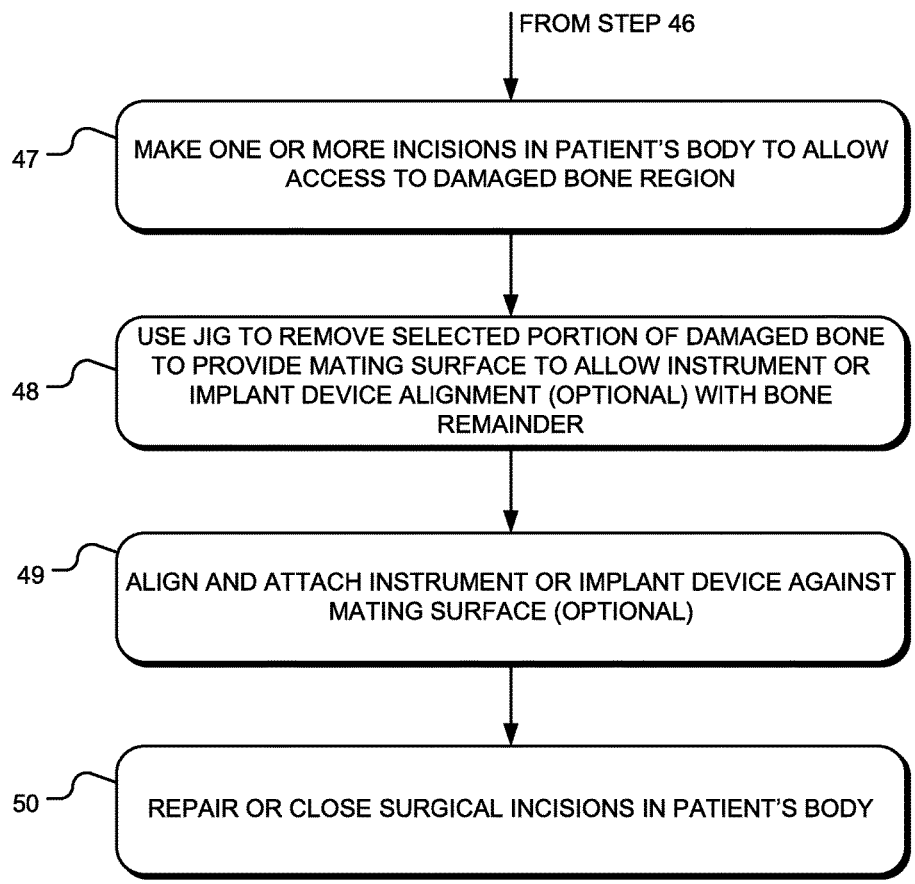

FIGS. 4A/4B are a flow chart for practicing the invention. In step 41, a damaged region of a bone, or of one or more adjacent bones, is optionally identified. In step 42, a CT image is formed of the damaged bone region and, preferably, of all portions of each bone involved in the damaged region (e.g., proximal end of the femur and/or distal end of the tibia). For example, if a femur-tibia connection at a knee is damaged, a CT image of the full length of the femur and of the full length of the tibia are preferably formed, including the ends of these bones that are not involved in the damaged bone region. In step 43, location coordinate values of each of a sequence of spaced apart surface points on each bone in the damaged bone region are determined from the CT image. Optionally, these location coordinates are referenced to an absolute coordinate system associated with the damaged bone region.

In step 44, a model of a bone surface in the damaged bone region is estimated or computed, using a mathematical method described herein or another appropriate method. Optionally, the surface points are used to subdivide the bone surface in the damaged bone region into a sequence of polygons P, preferably triangles and/or quadrilaterals, as part of the surface modeling process. At least three approaches are available here.

In a first approach, a mathematical model of the surface is developed ion that matches, as closely as possible, the coordinate values $(x_n, y_n, z_n)$ of each of the sequence of surface location points provided by the CT image. Here, the bone surface may be modeled within each of the sequence of polygons P, and the sequence of approximations can be treated collectively for the bone surface as a whole; or the bone surface may be modeled in the large by a single polynomial, trigonometric series or other function set in appropriate location coordinates, such as Cartesian coordinates $(x,y,z)$.

In a second approach, a surface normal at a selected point within each of the sequence of polygons P is measured or otherwise provided, using the CT image information, and a surface portion within that polygon is determined for which the surface normal matches, as closely as possible, the CT image-provided surface normal at the selected point. In a third approach, use of surface point locations and surface normal vectors are combined.

In step 45, the mathematical model determined for the bone surface in the damaged bone region is used, as part of a production file, to generate automated instructions for fabricating a cutting jig and an implant device (optional) for each of the femur and the tibia. In step 46, the cutting jig and the implant device (optional) are fabricated, using the production file cutting jig preferably includes a planar surface to allow the implant device to mate with and align with the bone.

In step 47, one or more incisions is made on the patient's body to expose the damaged bone region and to allow access to the damaged bone region. The cutting jig is used to remove a selected end portion of the bone and to provide an exposed planar surface of the bone remainder.

In step 48, a selected portion of the damaged bone is removed, using the cutting jig, to provide a planar surface against which an implant device will be (optionally) fitted.

In step 49, the implant device is optionally fitted to, and secured against, the planar surface of the bone remainder, and alignment of the implant device with one or more bone axes and implant device attachment is implemented. In step 50, the surgical incisions in the patient's body are repaired; the patient's body is "sewn up" (once). Only one surgical procedure, with its concomitant incisions and cutting, is required here, and this surgical procedure requires an estimated 20-25 minutes to complete, including bone end remainder and implant device alignment and attachment.

The following is a more detailed discussion of practice of the invention for TJA, where the damaged bone region is a patent's knee.

Figure 5:
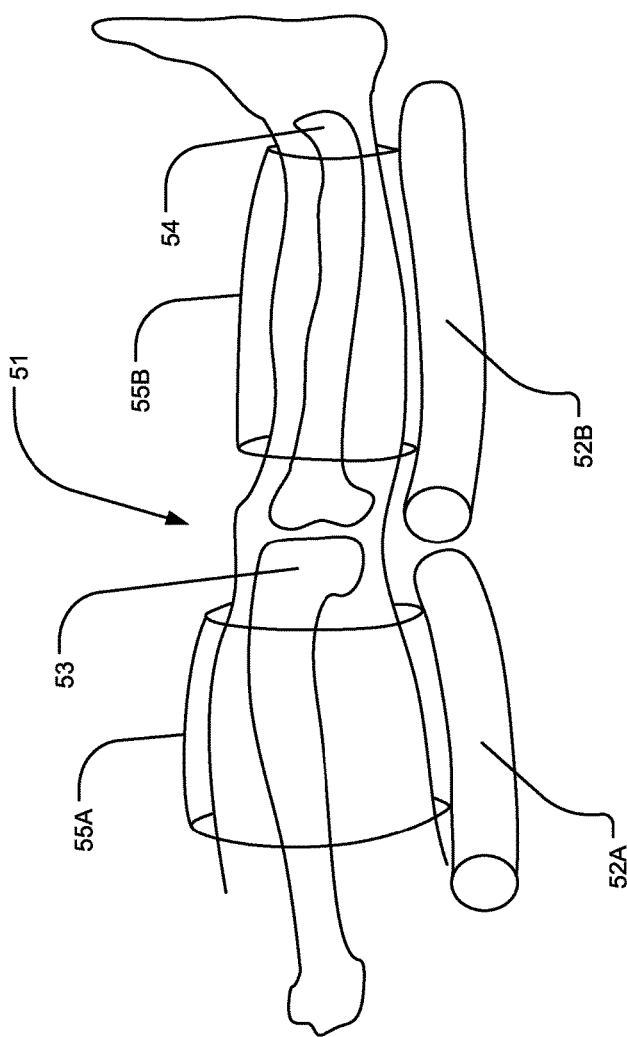
FIG. 5 illustrates a non-invasive bone positioning device used in pre-operative planning according to the invention.
Figure 6:
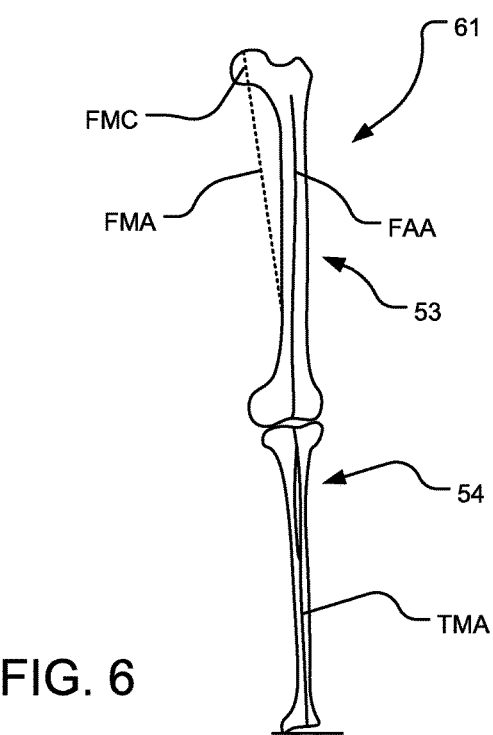
FIG. 6 illustrates three axes of interest on a femur and a tibia.

Stage I:

A non-invasive bone fixturing device 51 is provided (not requiring cutting or piercing of the skin), including a system of rigid bars, 52A and 52B, strapped to and immobilizing the patient's femur 53 and tibia 54 by a plurality of elastic steps, 55A and 55B, as shown in FIG. 5. Optionally, the bone fixturing device 51 is also used as a reference frame. The damaged knee (or other joint) of the patient is CT scanned and processed into a computer file, using a selected reference frame. With the exception of severely abnormal or fractured knee joints, the CT scan concentrates on pertinent areas, in and around the damaged bone region, that will assist in determining the femoral mechanical axis (FMA), femoral mechanical center (FMC), femoral anatomical axis (FAA) and tibial mechanical axis (TMA), as shown in FIGS. 5 and 6. The CT image data, including data conversion into a 3-D geometric format, are received by a computer, and the system automatically performs the following: (1) A 3D conversion algorithm is utilized to provide 3D graphical representation of the knee components, where the algorithm provides optimal graphical representation for the knee implants' planning process as well as downstream production applications; and (2) The system software analyzes bone motion detection and re-configuration algorithms. If bone motion is detected, the system analyzes and re-configures the bones (here, femur 53 and tibia 54) with respect to the bone positions. If too much movement is detected, the system recommends re-scanning the knee to provide a new image.

Figure 7:
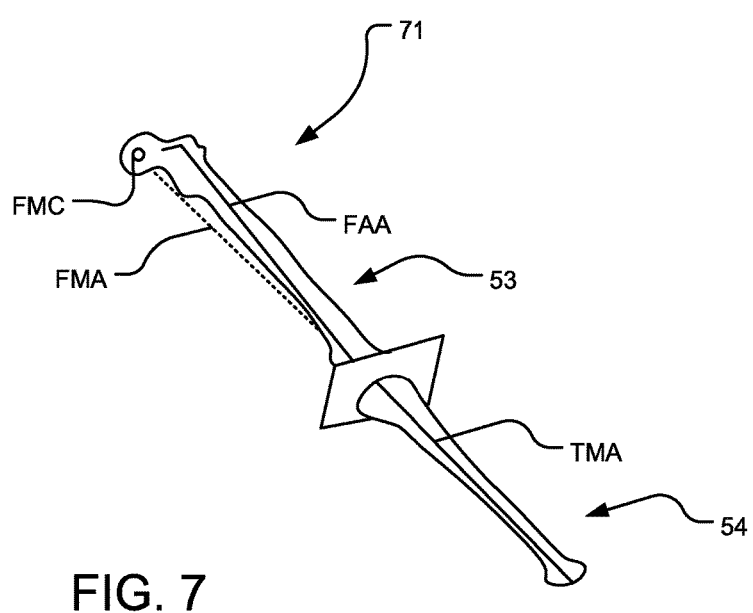
FIG. 7 illustrates pre-operative planning and measuring according to the invention.

Stage II:

The 2D and 3D models of the knee from Stage I are viewable on the preoperative plug system PC display as well as a library LINK of the femoral and tibial knee implant components. The library includes 3D models of various size implants and other ancillary parts. The names of the implant manufacturers and manufacturer's surgical criteria and optimum alignment conditions for implant installation will also be available. As an example, using the system to determine the FMA, the surgeon may execute the following sequence: (1) select the center of the femoral head with an icon; (2) select the center of the knee (other end of the femur) with another icon; and (3) connect the two icons with a straight line. This defines an FMA, one of the axes, as illustrated in FIGS. 5, 6 and 7. If the surgeon has a preferred way of determining the FMA, the surgeon has the flexibility to use any desired graphical method. For ascertaining the FAA and the TMA, also shown in FIG. 7, similar techniques are implemented.

Similar to commercially available graphic software, the preoperative planning system includes capabilities for enlargement, shrinking, panning, zooming, rotating, etc. As shown in FIG. 7, a plane 72, perpendicular to FMA, represents a transverse cut of the distal femur 53 (and of the proximal tibia 54); this information is used to create a slot for transverse cutting during the actual surgery.

The system allows a surgeon to perform the following: (1) check the results of the pre-operative planning to avoid or minimize the consequences of mistakes; and (2) simulate and recommend other available orthopedic theories, techniques and case studies, i.e., for bowed legs and fractured knees, which will be based on recent literature, surveys and widely accepted knee kinematics and alignment theories. This particular portion of the system is optional; the surgeon makes the final decisions in implant planning.

Stage III:

The system generates a production file, including a machining or fabrication file, based upon information of the planned position and alignment of the femoral and tibial components from the previous stage. This file is used to control a production machine that fabricates the patient-specific jigs for both femoral and tibial aspects of the knee. These unique jigs, an example of which is shown in FIGS. 8A/B/C, implement transfer and use of information between preoperative planning and surgery and allow a member of the surgery team to provide a clean, precise slice and an exposed planar surface of the remainder of the bone. The production file creates one or more selected internal (mating) surfaces of the exterior surface profile for the damaged knee surface geometry, for accurate patient-specific mating between the jig and the remainder of the patient's distal femur. In addition, the production file creates a transversely oriented slot and cutting instrument guide for a transverse cutting process. These features are optionally created with respect to the inter-condylar aperture (FAA) as a reference point. Accurate mating between the jig and the distal end of the femur ensures the accurate translation and angular position of the slot as planned in STAGE II. This provides the surgeon with access to a transverse cut on the distal femur, which establishes the correct alignments and provides reference planes for assembling manual instrumentation for the rest of the cuts required for knee implant installation.

Figure 8C:
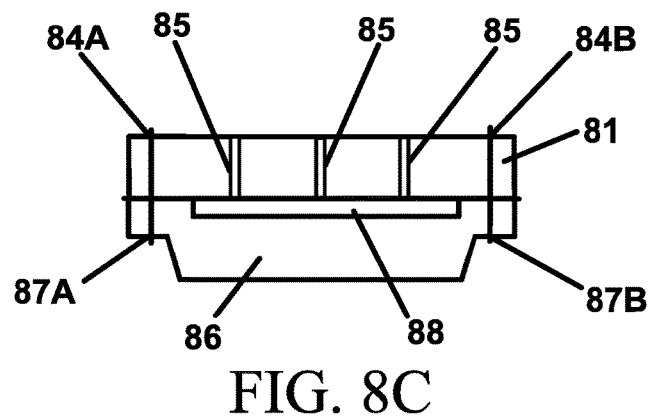
FIGS. 8A/8B/8C are schematic views of a surgical implant device for TKA, prepared according to the invention.

FIGS. 8A and 8B are perspective views of a cutting jig, 81 and 86, fabricated according to the invention. The model of the damaged bone region is used to define a selected region 82 to be removed from a block 83 of hardened material (preferably a biocompatible plastic) that is a first component 81 of the cutting jig. The region 82 is selected so that the damaged bone region will fit snugly into the hollowed-out region in the block 83. First and second lateral projections, 84A and 84B, are provided on the block 83, with each projection having an aperture that is approximately perpendicular to an initial surface 83S of the block 83. A second component 86 of the cutting jig includes third and fourth projections, 87A and 87B, that mate with the respective first and second projections, 84A and 84B, of the first component 81. Apertures in the third and fourth projections, 87A and 87B, mate with and are aligned with the apertures in the first and second projections, 84A and 84B, respectively. When the first jig component 81 is mated with the second jig component 86, a small, transversely oriented gap 88 is defined between the first and second jig components, into which a cutting instrument can be inserted to cut off and remove a damaged region of the bone, as illustrated in FIG. 8C. Drilling holes 85 extending through the first component 81 are also seen in FIG. 8C. After a transverse cut is made, using the jig 81/86, a first aperture is formed in the remainder of the bone, along the bone longitudinal axis, and one or more additional apertures are formed, parallel to and spaced apart from the first aperture. These apertures are used to align an implant device with the bone remainder.

Figure 9:
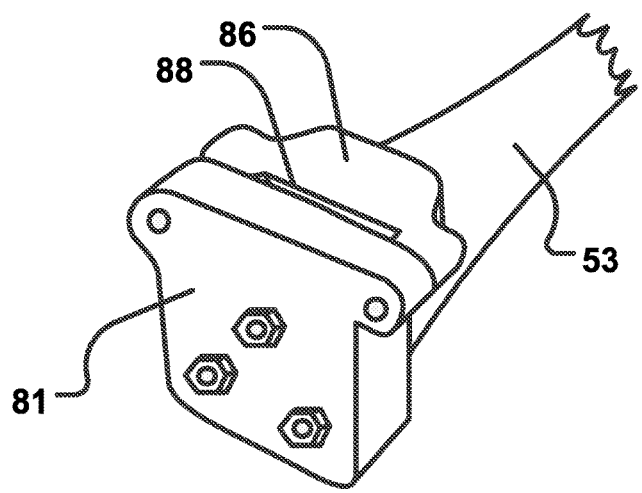
FIG. 9 is a schematic view of mating of a component of the implant device and a body part (femur) of the patient.

The system automatically determines the correct size of the jigs for the distal end of the femur and the proximal end of the tibia (53 and 54 in FIG. 5). The system includes an algorithm for determining optimum mating conditions through volume and tolerance/interference checks between the patient knee and the jigs. FIG. 9 illustrates how the virtual mating of the patient-specific jig components, 81 and 86, to the distal femur 53 are displayed on a PC screen. The system includes an algorithm that performs the following functions: (1) generation of efficient production processes; and (2) determination of production parameter conditions. In this stage, no surgeon or user intervention occurs, and the production file along with CT image file is transferred from the hospital planning station to a rapid production floor through a secure inter-net connection or other methods.

Stage IV:

The patient-specific jigs (optionally disposable) are fabricated with rapid production machines. The fabricated features are inspected through a quality control procedure. During the production process, reporting status and error conditions are critical. In order to achieve high quality surface mating, the accommodation of control modules that actively monitor and adjust the machining process should be considered. The system automatically executes and provides information pertinent to the production and inspection processes. The quality procedure involves monitoring and verification of (1) the profile surface of the jigs compared to the profile of the knee surface determined from the CT image and (2) translation and angular positioning of the machined features such as transverse and tibial cutting slots. Finally, the jigs are cleaned, sterilized (optional), labeled, packaged and delivered to the hospital. As yet, no cutting of the patient's body bas occurred.

Modeling of a Bone Surface

Other inventions require so called shape-based registration that the shapes of the bone surface model generated from a pre-operative image are matched to surface data points collected during a first phase of surgery. This surface matching method requires finding a mapping relation (transformation matrix) between bone surface data points and the bone surface model. Therefore, the accuracy of registration process depends on the number of points and distance between each point. Once the mapping relation is found, the pre-operative plan can be performed based on the mapping relation during the surgery. The mapping relation between surface data points and the bone surface model from a preoperative image can provide surgeons with the pre-operative image based planning information needed for a successful surgery. A key to the success of this method is determination of an accurate bone surface representation of a preoperative image. The more accurate the bone surface model is, the more precise the position and alignment of the implant device.

This invention differs from other approaches in not requiring use of a registration process during actual surgery. The invention relies upon a virtual registration process for a bone surface mathematical model generated from a pre-operative, CT scanned image. In order to achieve this goal, the invention includes the interpolated deterministic data points as well as uncertainty associated with each point. This uncertainly information is critical for the production of surgical device (hardware) and surgical error analysis prior to surgery.

Several approaches can be used for virtual registration.

(1) Point-to-point mapping on the bone surface model. Virtual data points on the 3D CT bone surface are selected to accurately describe the distal femur and the proximal tibia in the damaged bone region. Based on the selected data points, virtual pins are introduced at selected surface points with corresponding coordinate values, such as (x,y,z), that are to be used to map the bone surface at these locations. The directions of all virtual pins are straight and may be parallel to, or transverse to, the femoral anatomical axis (FAA). No particular pin direction is required. A pin can point at each selected surface point in any direction, for example in a direction of a surface normal at that surface point. Once the pre-operative planning is completed, an implant device can be fabricated using available manufacturing techniques. The surgical hardware can be disposable or re-usable. During surgery, the implant device with pre-operative planning information, such as slot position and drilling hole locations, is placed on the distal femur. Custom mating between the surgical device and the distal (or proximal) bone surface ensures accurate mapping relation between the actual bone surface and the bone surface model. The more data points are selected, the more accurate surgical result is obtained.

(2) Surface normal vector mapping on the bone surface model. Sufficient virtual data points on the 3D CT image bone surface are selected to describe the geometry of the distal femur and the proximal tibia. Based on the selected data points, virtual pins and pin directions are introduced at the selected data points, with the direction of each virtual pin being normal to the surface at each selected point. The virtual pin directions are arbitrary, but a pin direction normal to the local surface is preferred. Once this pre-operative planning is completed, surgical device can be made using any available manufacturing techniques. The surgical hardware, including jig, can be disposable of re-usable. During surgery, the implant device (patient-specific or off-the-shelf), including pre-operative planning information, such as slot position, drilling hole locations is fabricated and placed on the distal femur. Custom mating between the implant device and the distal bone surface ensures accurate mapping relation between the actual bone surface and the bone surface model. A sufficient number of source point locations and corresponding normal vector component values are determined (preferably five or more) to provide an accurate model of the bone surface.

(3) Local surface mapping on the bone surface model. Several local mating virtual areas on the 3D CT image bone surface are selected to describe a geometry of the distal femur and proximal tibia. The local surface-to-surface mapping is equivalent to case (2), surface normal vector mapping, but uses a significantly larger number of data points. Once this pre-operative planning is completed, surgical device can be made using any available manufacturing techniques. The surgical hardware can be disposable or re-usable. During surgery, the implant device with pre-operative planning information, such as slot position, drilling hole locations is placed on the distal femur. Custom mating between the implant device and the distal bone surface ensures accurate mapping relation between the actual bone surface and the bone surface model. Use of a local area surface mapping approach can significantly increase the accuracy and reliability of the surgery.

(4) Global surface mapping on the bone surface model. One global mating virtual area on the 3D CT image bone surface is determined to describe the geometry of the distal femur and proximal tibia. A global a surface-to-surface mapping is employed, and this approach is equivalent to case (3), the local surface mapping on the bone surface model, with the increased surface contact areas. Once this pre-operative planning is completed, surgical device can be made using any available manufacturing techniques. The surgical hardware can be disposable or re-usable. During surgery, the implant device with pre-operative planning information, such as slot position, drilling hole locations is placed on the distal femur. Custom mating between the implant device and the distal bone surface ensures accurate mapping relation between the actual bone surface and the bone surface model.

Precise pre-operative planning is essential for a successful TJA. Several techniques of CT-based pre-operative planning have been developed. The system allows the surgeon to develop a plan of component placement in TJA. Surgeons can check the plan that they have made by referring to the geometric relationship with respect to the implant.

A repaired knee joint, or other joint, may fail prematurely, for any of several reasons. Instability of the implant device, due to kinematic misalignment, may cause such failure and may require performance of a revision TKA. This is a delicate surgical procedure in which additional bone loss, due to realignment, must be minimized. A revision TKA begins with removal of the original implant device and of any bone cement remaining between the implant device and the exposed bone surface. During pre-operative planning, a bone surface image can be formed and preserved, not including the bone cement and implant device surfaces. Based on his (preserved) image data, another patient-specific jig is fabricated with its own (corrected) cutting slot, using the techniques discussed for primary or original TKA. Because all bone surfaces are already shaped due to the earlier primary TKA procedure, use of a surface-to-surface mapping would be appropriate here.

Mathematical Details of Bone Surface Matching.

Figure 10A:
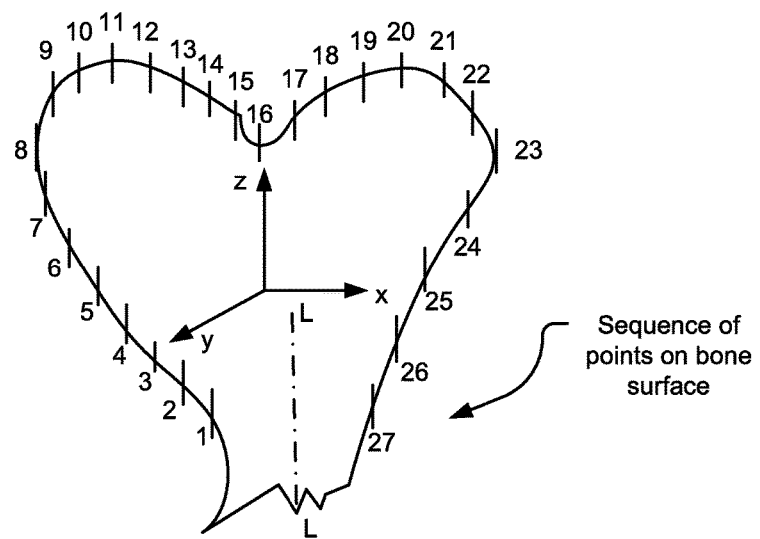
FIGS. 10A, 10B, 11 and 12 illustrate a procedure for estimating a local shape function for point-to-point matching on a surface.
Figure 10B:
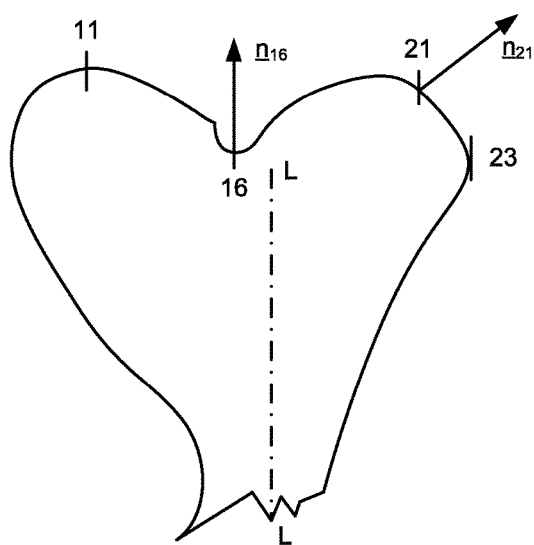

FIGS. 10A and 10B are views of a slice of an end of a bone 151, such as a femur or a tibia, that is analyzed using a CT scan to provide an estimate of a surface shape function $z=f_s(x,y)$ that accurately describes an end portion of the bone. An (x,y,z) Cartesian coordinate system is shown imposed on the bone 151, with the z-axis oriented approximately parallel to a longitudinal axis LL of the bone, and the slice optionally corresponds to a plane a'x+b'y=constant; for convenience in notation, it may be assumed here that a=0. In FIG. 10A, a sequence of spaced apart points with coordinates $(x_n,y_n,z_n)$ (n=1, 2, . . . , 27) are shown for the slice.

In a first approximation, first and second sequences of incremental ratios or derivative approximations $$(\Delta x/\Delta z)_n = (x_{n+1}-x_n)/(z_{n+1}-z_n), \quad (1)$$

$$(\Delta y/\Delta z)_n = (y_{n+1}-y_n)/(z_{n+1}-z_n), \quad (2)$$

are computed, using a linear approximation ratio for each of the derivatives. The first sequence of derivatives $\{(\Delta x/\Delta z)_n\}_n$ is then subdivided into a group of one or more mutually exclusive sub-sequences $\{(\Delta x/\Delta z)_{nk}\}_k$ (k=1, . . . , K), with each sub-sequence having a consecutive subset of the ratios $(\Delta x/\Delta z)_n$ with monotonically increasing, or monotonically decreasing, numerical values for the derivatives. In a similar manner, the second sequence of derivatives $\{(\Delta y/\Delta z)_m\}_m$ is then sub-divided into a group of one or more mutually exclusive sub-sequences $\{(\Delta y/\Delta z)_{mj}\}_j$ (j=1, . . . , J), with each sub-sequence having a consecutive subset of the ratios $(\Delta y/\Delta z)_m$ with monotonically increasing, or monotonically decreasing, numerical values for the derivatives. Within each of the regions where the derivatives are monotonic, a simplified approximation to the local surface can be used.

The preceding equations are used to define regions of mating along the femoral anatomical axis. A change in slope from monotonic increase to decrease, or from monotonic decrease to increase, indicates that mating is no longer possible with respect to the FAA.

Figure 11:
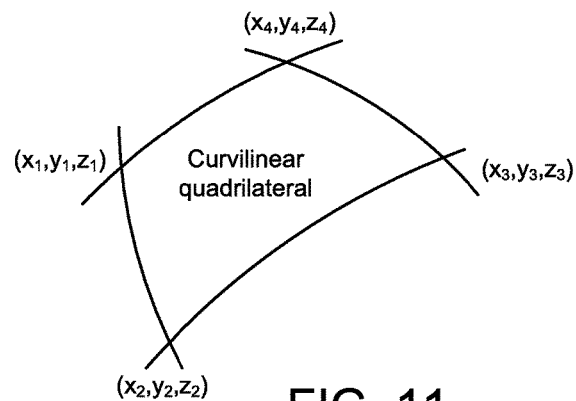

(1) Point-to-point bone surface mapping. Consider a quadrilateral Q(1,2,3,4), having a non-zero enclosed area and defined by four adjacent but distinct points, having coordinates $(x_n,y_n,z_n)$ (n=1, 2, 3, 4), as illustrated in FIG. 11, that are determined, using a CT scan, to lie on a surface BS of the bone 151 in FIGS. 10A and 10B. One goal is to determine a shape function $z=f_s(x,y)$ that is differentiable within a polygonal region and that satisfies $z_n=f_s(x_n,y_n)$ for n=1, 2, 3, 4. Consider first a situation in which no two or more x-coordinate values $x_n$ are equal and no two or more y-coordinate values $y_n$ are equal, referred to as a (4,4)

situation, indicating that four distinct x-coordinates values and four distinct y-coordinate values are needed to define the quadrilateral Q(1,2,3,4). In this (4,4) situation, one suitable shape function for a quadrilateral grid is $$z = f_s(x,y;4;4;qu) = z_1(x-x_2)(x-x_3)(x-x_4)(y-y_2)(y-y_3)(y-y_4)/(d_x(1;2,3,4) \cdot d_y(1;2,3,4)) + z_2(x-x_1)(x-x_3)(x-x_4)(y-y_1)(y-y_3)(y-y_4)/(d_x(2;1,3,4) \cdot d_y(2;1,3,4)) + z_3(x-x_1)(x-x_2)(x-x_4)(y-y_1)(y-y_2)(y-y_4)/(d_x(3;1,2,4) \cdot d_y(3;1,2,4)) + z_4(x-x_1)(x-x_2)(x-x_3)(y-y_1)(y-y_2)(y-y_3)/(d_x(4;1,2,3) \cdot d_y(4;1,2,3)),$$ (3)

$$d_x(a;b,c,d) = (x_a-x_b) \cdot (x_a-x_c) \cdot (x_a-x_d),$$ (4)

$$d_y(a;b,c,d) = (y_a-y_b) \cdot (y_a-y_c) \cdot (y_a-y_d).$$ (5)

At each of the four locations $(x_n, y_n, z_n)$, three of the four terms in the expression for $z=f_s(x,y;4;4;qu)$ vanish, and $f_s(x_n, y_n;4;4;qu)=z_n$.

In a (3,4) situation, only three of the four x-coordinate values are different (e.g., $x3 \neq x1 = x2 \neq x4 \neq x3$), but all four of the y-coordinate values are different from each other. In this (3,4) situation, the shape function is defined to be:

$$z = f_s(x,y;3;4;qu) = z_1(x-x_3)(x-x_4)(y-y_2)(y-y_3)(y-y_4)/(d_x(1;3,4) \cdot d_y(1;2,3,4)) + z_2(x-x_3)(x-x_4)(y-y_1)(y-y_3)(y-y_4)/(d_x(2;3,4) \cdot d_y(2;1,3,4)) + z_3(x-x_1)(x-x_4)(y-y_1)(y-y_2)(y-y_4)/(d_x(3;1,4) \cdot d_y(3;1,2,4)) + z_4(x-x_1)(x-x_3)(y-y_1)(y-y_2)(y-y_3)/(d_x(4;1,3) \cdot d_y(4;1,2,3)),$$ (6)

$$d_x(a;b,c) = (x_a-x_b) \cdot (x_a-x_c),$$ (7)

$$d_y(a;b,c) = (y_a-y_b) \cdot (y_a-y_c).$$ (8)

For the (4,3) situation, with four distinct x-coordinates values and only three distinct y-coordinate values, the shape function $z=f_s(x,y;4;3;qu)$ is defined analogous to the shape function $z=f_s(x,y;3;4;qu)$ in Eq. (6).

In a (2,4) situation, only two of the four x-coordinate values are different (e.g., $x1=x2 \neq x3=x4$), but all four of the y-coordinate values are different from each other. In this (2,4) situation, the shape function is defined to be:

$$z = f_s(x,y;2;4;qu) = z_1(x-x_3)(y-y_2)(y-y_3)(y-y_4)/(d_x(1;3) \cdot d_y(1;2,3,4)) + z_2(x-x_3)(y-y_1)(y-y_3)(y-y_4)/(d_x(2;3) \cdot d_y(2;1,3,4)) + z_3(x-x_1)(y-y_1)(y-y_2)(y-y_4)/(d_x(3;1) \cdot d_y(3;1,2,4)) + z_4(x-x_1)(y-y_1)(y-y_2)(y-y_3)/(d_x(4;1) \cdot d_y(4;1,2,3)),$$ (9)

$$d_x(a;b) = (x_a-x_b),$$ (10)

$$d_y(a;b) = (y_a-y_b).$$ (11)

For the (4,2) situation, with four distinct x-coordinates values and only two distinct y-coordinate values, the shape function $z=f_s(x,y;4;2;qu)$ is defined analogous to the shape function $z=f_s(x,y;2;4;qu)$ in Eq. (9).

In a (3,3) situation, only three of the x-coordinate values are different (e.g., $x3 \neq x1 = x2 \neq x4 \neq x3$), and only three of the y-coordinate values are different (e.g., $y4 \neq y1 = y2 = y3 \neq y4$). In this (3,3) situation, the shape function is defined to be:

$$z = f_s(x,y;3;3;qu) = z_1(x-x_3)(x-x_4)(y-y_2)(y-y_4)/(d_x(1;3,4) \cdot d_y(1;2,4)) + z_2(x-x_3)(x-x_4)(y-y_1)(y-y_4)/(d_x(2;3,4) \cdot d_y(2;1,4)) + z_3(x-x_1)(x-x_4)(y-y_1)(y-y_4)/(d_x(3;1,4) \cdot d_y(3;1,4)) + z_4(x-x_1)(x-x_3)(y-y_1)(y-y_2)/(d_x(4;1,3) \cdot d_y(4;1,2)),$$ (12)

In a (2,3) situation, two of the four x-coordinate values are different (e.g., $x1=x2 \neq x3=x4$), and three of the y-coordinate values are different from each other (e.g., $y1 \neq y2=y3 \neq y4 \neq y3$). In this (2,3) situation, the shape function is defined to be:

$$z = f_s(x,y;2;3;qu) = z_1(x-x_3)(y-y_2)(y-y_4)/(d_x(1;3) \cdot d_y(1;2,4)) + z_2(x-x_3)(y-y_1)(y-y_4)/(d_x(2;3) \cdot d_y(2;3,4)) + z_3(x-x_1)(y-y_1)(y-y_4)/(d_x(3;1) \cdot d_y(3;1,4)) + z_4(x-x_1)(y-y_1)(y-y_2)/(d_x(4;1) \cdot d_y(4;1,2)),$$ (13)

For the (3,2) situation, with three distinct x-coordinates values and two distinct y-coordinate values, the shape function $z=f_s(x,y;3;2;qu)$ is defined analogous to the shape function $z=f_s(x,y;2;3;qu)$ in Eq. (13).

In a (2,2) situation, two of the four x-coordinate values are different (e.g., $x1=x2 \neq x3=x4$), and two of the y-coordinate values are different (e.g., $y4=y1 \neq y2=y3$). In this (2,2) situation, the shape function is defined to be:

$$z = f_s(x,y;2;2;qu) = z_1(x-x_3)(y-y_2)/(d_x(1;3) \cdot d_y(1;2)) + z_2(x-x_3)(y-y_1)/(d_x(2;3) \cdot d_y(2;1)) + z_3(x-x_1)(y-y_1)/(d_x(3;1) \cdot d_y(3;1)) + z_4(x-x_1)(y-y_2)/(d_x(4;1) \cdot d_y(4;2)),$$ (14)

Figure 12:
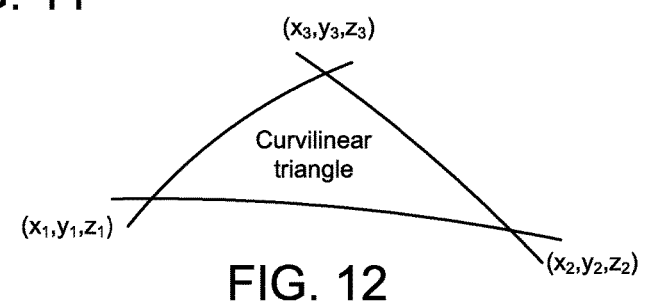

More generally, the quadrilateral Q(1,2,3,4) can be replaced by an M-vertex polygon (M≥3) having non-zero included numerical area, and a shape function for this polygon is determined by analogy to the preceding development. The simplest polygon here, having the lowest corresponding polynomial degree in x and y, is a triangle (M=3). The particular shape function used will depend upon the configuration of the polygon relative to the coordinate axes. For definiteness, it may be assumed here that the bone surface BS is divided by a grid of quadrilaterals (or triangles) and that the coordinate values $(x_n, y_n, z_n)$ (n=1, 2, 3, 4) of the vertices are known from analysis of the CT scan.

Where a sequence of triangles, rather than a sequence of quadrilaterals, is used to define a grid for the bone surface, as illustrated in FIG. 12, three coordinate triples $(x_n, y_n, z_n)$ (n=1, 2, 3) are provided to define each such triangle. In a (3,3) situation, all three of the x-coordinate values are different ($x3 \neq x1 \neq x2 \neq x3$), and all three of the y-coordinate values are different ($y3 \neq y1 \neq y2 \neq y3$). In this (3,3) situation, the shape function for a triangular grid is defined to be:

$$z = f_s(x,y;3;3;tr) = z_1(x-x_2)(x-x_3)(y-y_2)(y-y_3)/(d_x(1;2,3) \cdot d_y(1;2,3)) + z_2(x-x_1)(x-x_3)(y-y_1)(y-y_3)/(d_x(2;1,3) \cdot d_y(2;1,3)) + z_3(x-x_1)(x-x_2)(y-y_1)(y-y_2)/(d_x(3;1,2) \cdot d_y(3;1,2)).$$ (15)

In a (2,3) situation, where only two x-coordinate values are different (e.g., $x1=x2 \neq x3$) and all three y-coordinate values are different, the shape function is defined to be:

$$z = f_s(x,y;2;3;tr) = z_1(x-x_3)(y-y_2)(y-y_3)/(d_x(1;3) \cdot d_y(1;2,3)) + z_2(x-x_3)(y-y_1)(y-y_3)/(d_x(2;3) \cdot d_y(2;1,3)) + z_3(x-x_1)(y-y_1)(y-y_2)/(d_x(3;1) \cdot d_y(3;1,2)).$$ (16)

For the (3,2) situation, with three distinct x-coordinates values and two distinct y-coordinate values, the shape function $z=f_s(x,y;3;2;tr)$ is defined analogous to the shape function $z=f_s(x,y;2;3;tr)$ in Eq. (16).

In a (2,2) situation, two of the three x-coordinate values are different (e.g., $x1=x2 \neq x3$), and two of the three y-coordinate values are different (e.g., $y1 \neq y2=y3$). In this (2,2) situation, the shape function is defined to be:

$$z = f_s(x,y;2;2;tr) = z_1(x-x_3)(y-y_2)/(d_x(1;3) \cdot d_y(1;2)) + z_2(x-x_3)(y-y_1)/(d_x(2;3) \cdot d_y(2;1)) + z_3(x-x_1)(y-y_1)/(d_x(3;1) \cdot d_y(3;1)).$$ (17)

Where a quadrilateral grid is used and, for a given quadrilateral, precisely M x-coordinate values are different and precisely N y-coordinate values are different (2≤M≤4; 2≤N≤4), the shape function is a polynomial of degree M−1 in x and of degree N−1 in y. Utilizing the theory of equations and roots of equations, one can show that the shape function defined in this manner for a quadrilateral, satisfying $f_s(x_n, y_n; M; N; qu) = z_n$ (n=1, 2, 3, 4) and having minimal polynomial degree, is unique, although the polynomial itself may be expressed in different, equivalent ways.

Where a triangular grid is used and, for a given triangular, precisely M x-coordinate values are different and precisely N y-coordinate values are different (2≤M≤3; 2≤N≤3), the shape function is a polynomial of degree M−1 in x and of degree N−1 in y. Utilizing the theory of equations and roots of equations, one can show that the shape function defined in this manner for a quadrilateral, satisfying $f_s(x_n,y_n;M;N;tr)=z_n$ (n=1, 2, 3) and having minimal polynomial degree, is unique, although the polynomial itself may be expressed in different, equivalent ways. The shape function polynomial for a triangular grid has smaller polynomial degree in x and in y (as small as degree 1 in each of x and in y) than the corresponding shape function polynomial for a quadrilateral grid.

The shape function, $f_s(x,y;M;N;tr)$ or $f_s(x,y;M;N;qu)$, may be used as is to describe a minimal polynomial surface for a particular polygon satisfying $f_s(x_n,y_n,M;N;tr$ or $qu)=z_n$. If desired, the grid adopted may include a mixture of triangles and quadrilaterals, with each such polygon having its own shape function. That is, if the grid includes a total of K polygons (e.g., triangles and/or quadrilaterals), a total of K shape functions are defined, using the preceding mathematical construction.

(2) Bone surface normal mapping. The components of a vector n(x,y) normal to the bone surface defined by the shape function for a particular quadrilateral are determined to be:

$$n(x,y)=\{\partial f_s/\partial x, \partial f_s/\partial y, -1\}, \quad (18)$$

where the vector components can be, but need not be, normalized to unit length, if desire. These normal vector components can be used to determine the local surface normal n(x,y) for an implant device that approximates as closely as possible the bone surface BS imaged by the CT scan. Again, if the grid includes a total of K polygons (e.g., triangles and/or quadrilaterals), a total of up to K shape functions are defined, using the preceding mathematical construction, and a surface normal at a selected location within each polygon is computed.

Figure 13:
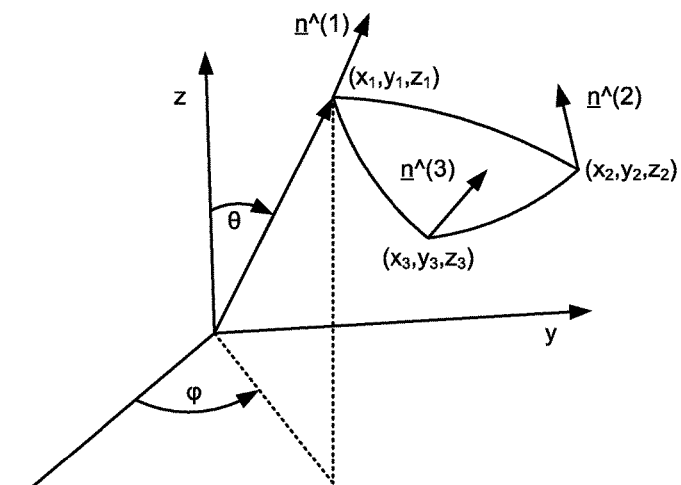
FIG. 13 illustrates a procedure for estimating a local surface for surface normal vector matching.

FIG. 13 illustrates a surface element SE, defined by three spaced apart locations with Cartesian coordinates $(x_m,y_m,z_m)$ (m=1, 2, 3), with each location having a surface normal of unit length n̂(m) that is specified, for example, by information from the CT image. With reference to a spherical coordinate system (r,θ,φ) that is aligned as shown with the Cartesian coordinate system, the vector components of a unit-length normal at a given location are expressible as:

$$\hat{n}=(\cos\phi\sin\theta, \sin\phi\sin\theta, \cos\theta). \quad (19)$$

A local surface element defined by the three locations $(x_m,y_m,z_m)$ is approximated by a surface element of an ellipsoid that is rotated by an angle ψ in the (x,y)-plane relative to the x-coordinate axis:

$$\{(x-x0)\cos\psi+(y-y0)\sin\psi\}^2/a^2+\{-(x-x0)\sin\psi+(y-y0)\cos\psi\}^2/b^2+(z-z0)^2/c^2=1, \quad (20)$$

where a, b and c are three positive numbers and x0, y0 and z0 are three coordinate values, and ψ is a rotation angle, as yet unspecified. Locally, the ellipsoid surface can be re-expressed in functional form as:

$$z(x,y)=z0\pm c\{1-u^2-v^2\}^{1/2}, \quad (21)$$

$$\partial z/\partial x=-(\pm)(c/a)u/\{1-u^2-v^2\}^{1/2}, \quad (22)$$

$$\partial z/\partial y=-(\pm)(c/b)v/\{1-u^2-v^2\}^{1/2}, \quad (23)$$

$$u=\{(x-x0)\cos\psi+(y-y0)\sin\psi\}/a, \quad (24)$$

$$v=\{-(x-x0)\sin\psi+(y-y0)\cos\psi\}/b. \quad (25)$$

The expressions for ∂z/∂x and ∂z/∂y are strictly monotonic (increasing or decreasing) in each of the variables u and v and range from −∞ to +∞ so that, for any pair of real numbers (w1,w2), unique values u and v can be found for Eqs. (22) and (23) for which ∂z/∂x=w1 and ∂z/∂y=w2. Vector components for a unit-length normal vector for the surface z(x,y) are expressible as:

$$\hat{n}=(\pm(c/a)u, \pm(c/b)v, -\{1-(c/a)^2u^2-(c/b)^2v^2\}^{1/2}), \quad (26)$$

and unit-length surface normal vectors n̂(m) are to be matched at three locations, $(x,y,z)=(x_m,y_m,z_m)$. Matching of the third of these three vector components is automatic (apart from the signum) for a unit-length vector. These vector components matching requirements are expressed as:

$$(c/a)u_m=c'\{(x_m-x0)\cos\psi+(y_m-y0)\sin\psi\}/a^2=\cos\phi_m\cdot\sin\theta_m, \quad (27A)$$

$$(c/b)v_m=c'\{-(x_m-x0)\sin\psi+(y_m-y0)\cos\psi\}/b^2=\sin\phi_m\cdot\sin\theta_m, \quad (27B)$$

(m=1, 2, 3), where the right hand expressions are specified or measured values. Equations (27A) and (27B) can also be rotated and thereby expressed in the form:

$$x_m-x0(a^2/c)\cos\psi\cos\phi_m\sin\theta_m-(b^2/c)\sin\psi\sin\phi_m\sin\theta_m, \quad (28A)$$

$$y_m-y0(a^2/c)\sin\psi\cos\phi_m\sin\theta_m+(b^2/c)\cos\psi\sin\phi_m\sin\theta_m. \quad (28B)$$

Equations (27A) and (27B), or (28A) and (28B), are six equations in six explicit unknowns (x0, y0, ψ, a, b, c), and solutions can be found. Each surface element may have a different set of these unknowns, but two adjacent surface elements with a common vertex will have the same surface normal at that common vertex.

Once these six unknowns are determined, the ellipsoidal surface element extending between the three locations or vertices $(x_m,y_m,z_m)$ is defined, with a surface normal that varies continuously from a surface normal at one of these vertices to a surface normal at another of these vertices. These surface elements become part of a surface mosaic that provides a well-defined surface normal within the surface element interior. No matter which direction a surface element vertex is approached, from within any surface element that has that vertex, the surface normal vector will approach the same normal vector associated with that vertex. Although an ellipsoid, defined in Eq. (20) has been used here, any other three-dimensional conic, such as a saddle surface with at least one + sign replaced by a − sign in Eq. (20), can be used for surface normal matching in appropriate circumstances.

(3) Bone surface-to-surface mapping. A surface-to-surface mapping is an extension of bone surface normal mapping, using a significantly larger number of data points and surface normal vectors within selected regions.

Construction of a mathematical model of a portion of a bone surface has used polynomials in a Cartesian coordinate set (x,y,z). One could, as well, use a multi-coordinate Fourier series, expressed in cylindrical coordinates (r(θ,z), θ,z) or in another suitable coordinate set, for the location of selected points on a bone surface.

Any other suitable approach for point-to-point mapping and/or surface normal mapping can be used here to determine or estimate a mathematically expressed surface for a selected portion of a bone.

Although the example herein has focused on TJA for a patient's knee, the procedure is applicable to any other joint as well, such as a patient's hip, foot, toe, elbow, shoulder, wrist, finger or neck joint.

What is claimed is:

1. A system for use with an anchor and for performing an arthroplasty procedure on a patient bone having a surface feature, the bone having an axis associated with the bone, the axis identified in an analysis of the bone prior to using the jig assembly on the bone, the system comprising:
    a first component of a jig assembly comprising a mating surface and a guide hole, the mating surface being a surface negative of the surface feature of the patient bone, the mating surface configured to matingly engage the surface feature of the patient bone, the guide hole operably coupled to the mating surface of the positioning component and configured to guide the anchor into the patient bone when the mating surface matingly engages with the surface feature of the patient bone; and
    a second component of the jig assembly comprising a resection guide surface configured to guide a planar resection of the patient bone that is in a pre-planned orientation relative to the axis, the second component configured to couple to the first component.

2. The system of claim 1, wherein the surface feature in the patient bone is naturally occurring.

3. The system of claim 1, wherein the guide hole and the mating surface of the first component are part of a unitary construction.

4. The system of claim 1, wherein the first component and the second component are separate components configured to releasably couple.

5. The system of claim 4, wherein the first component and the second component are configured to releasably couple via engagement of a pair of openings in the second component.

6. The system of claim 1, wherein the patient bone is a femur.

7. The system of claim 6, wherein the surface feature of the patient bone is at a distal end of the femur.

8. The system of claim 1, wherein the resection guide surface is perpendicular to a mechanical axis of the bone when the anchor is in the patient bone.

9. The system of claim 8, wherein the mechanical axis is a femoral mechanical axis.

10. The system of claim 1, wherein the guide hole extends through the mating surface.

11. The system of claim 1, wherein the patient bone is a tibia.

12. A system for use with an elongate member and for performing an arthroplasty procedure on a patient bone having a surface engagement feature, the bone having an axis associated with the bone, the axis identified in an analysis of the bone prior to using the jig assembly on the bone, the system comprising:
    a first component of a jig assembly comprising a mating surface and a guide hole, the mating surface being a surface negative of the surface engagement feature of the patient bone, the mating surface configured to matingly engage the surface engagement feature of the patient bone, the guide hole extending through the mating surface of the positioning component and configured to guide the elongate member into the surface engagement feature of the patient bone when the mating surface matingly engages with the surface engagement feature of the patient bone; and
    a second component of the jig assembly comprising a resection guide surface configured to guide a planar resection of the patient bone that is in a pre-planned orientation relative to the axis, the second component configured to couple to the first component.

13. The system of claim 12, wherein the surface engagement feature in the patient bone is naturally occurring.

14. The system of claim 12, wherein the guide hole and the mating surface of the first component are part of a unitary construction.

15. The system of claim 12, wherein the first component and the second component are separate components configured to releasably couple.

16. The system of claim 15, wherein the first component and the second component are configured to releasably couple via engagement of a pair of openings in the second component.

17. The system of claim 12, wherein the patient bone is a femur.

18. The system of claim 17, wherein the surface engagement feature of the patient bone is at a distal end of the femur.

19. The system of claim 12, wherein the resection guide surface is perpendicular to a mechanical axis of the bone when the elongate member is in the patient bone.

20. The system of claim 19, wherein the mechanical axis is a femoral mechanical axis.

21. The system of claim 12, wherein the patient bone is a tibia.

22. A system for use with an elongate member and for performing an arthroplasty procedure on a patient bone having a surface engagement feature, the bone having an axis associated with the bone, the axis identified in an analysis of the bone prior to using the jig assembly on the bone, the system comprising:
    a first component of a jig assembly comprising a bone contacting surface and a guide hole extending through at least a portion of the bone contacting surface, the bone contacting surface being a mirror image of the surface engagement feature of the patient bone and existing in the first component prior to performing the arthroplasty procedure, the bone contacting surface configured to engage the surface engagement feature of the patient bone in a matching manner, the guide hole configured to guide the elongate member into the surface engagement feature of the patient bone when the bone contacting surface engages with the surface engagement feature of the patient bone in the matching manner; and
    a second component of the jig assembly comprising a resection guide surface configured to guide a planar resection of the patient bone that is in a pre-planned orientation relative to the axis, the second component configured to couple to the first component.

23. The system of claim 22, wherein the surface engagement feature in the patient bone is naturally occurring.

24. The system of claim 22, wherein the patient bone is a tibia.

25. The system of claim 22, wherein the first component and the second component are separate components configured to releasably couple.

26. The system of claim 25, wherein the first component and the second component are configured to releasably couple via engagement of a pair of openings in the second component.

27. The system of claim 22, wherein the patient bone is a femur.

28. The system of claim 27, wherein the surface engagement feature of the patient bone is at a distal end of the femur.

29. The system of claim 22, wherein the resection guide surface is perpendicular to a mechanical axis of the bone when the elongate member is in the patient bone.

30. The system of claim 29, wherein the mechanical axis is a femoral mechanical axis.

* * * * *